US009387312B2

(12) United States Patent
Smouse et al.

(10) Patent No.: US 9,387,312 B2
(45) Date of Patent: Jul. 12, 2016

(54) CONVERTIBLE NEPHROURETERAL CATHETER (71) Applicant: Brightwater Medical, Inc., Peoria Heights, IL (US)

(72) Inventors: Harry R. Smouse, Peoria, IL (US); Tim H. Williams, Campbell, CA (US)

(73) Assignee: Brightwater Medical, Inc., Peoria Heights, IL (US)

( * ) Notice: Subject to any disclaimer, the term of this patent is extended or adjusted under 35 U.S.C. 154(b) by 0 days.

(21) Appl. No.: 14/159,221

(22) Filed: Jan. 20, 2014

(65) Prior Publication Data

US 2014/0135941 A1 May 15, 2014

Related U.S. Application Data

(63) Continuation-in-part of application No. 12/559,946, filed on Sep. 15, 2009, now Pat. No. 8,657,884.

(60) Provisional application No. 61/096,902, filed on Sep. 15, 2008.

(51) Int. Cl.
*A61M 27/00* (2006.01)
*A61F 2/04* (2013.01)

(52) U.S. Cl.
CPC ........ *A61M 27/008* (2013.01); *A61F 2002/048* (2013.01); *A61M 2027/004* (2013.01)

(58) Field of Classification Search
CPC ................ A61F 2/04; A61F 2002/047; A61F 2002/048; A61M 27/002; A61M 27/008; A61M 2020/004
See application file for complete search history.

(56) References Cited

U.S. PATENT DOCUMENTS

| 3,996,938 A | 12/1976 | Clark, III |
| 4,350,161 A | 9/1982 | Davis, Jr. |
| 4,790,810 A | 12/1988 | Pugh, Jr. et al. |
| 4,830,003 A | 5/1989 | Wolff et al. |
| 5,002,560 A | 3/1991 | Machold et al. |

(Continued)

FOREIGN PATENT DOCUMENTS

WO    WO 88/05317 A1    7/1988

OTHER PUBLICATIONS

Notice of allowance dated Oct. 9, 2013 for U.S. Appl. No. 12/559,946.

(Continued)

*Primary Examiner* — Thomas J Sweet
*Assistant Examiner* — Daniel Bissing
(74) *Attorney, Agent, or Firm* — Wilson, Sonsini, Goodrich & Rosati (57) ABSTRACT

A nephroureteral catheter is provided that comprises a detachable portion such that when the detachable portion is removed, the catheter converts into an internal stent. The catheter includes a tube with two retention features, a detachable portion, and an inner tube. The inner tube is removably insertable into both the tube and the detachable portion, and a wire extends through at least a portion of a lumen of the inner tube and through the tube, to keep the pieces attached. The wire may be removed to remove the inner tube and then the detachable portion from the tube. When the detachable portion is attached to the tube, the catheter is a nephroureteral catheter. When the detachable portion is removed from the tube, the catheter becomes a stent.

21 Claims, 9 Drawing Sheets

(56) References Cited

U.S. PATENT DOCUMENTS

| | | |
|---|---|---|
| 5,019,090 A | 5/1991 | Pinchuk |
| 5,071,407 A | 12/1991 | Termin et al. |
| 5,250,069 A | 10/1993 | Nobuyoshi et al. |
| 5,456,667 A | 10/1995 | Ham et al. |
| 5,507,732 A | 4/1996 | Mcclure et al. |
| 5,507,751 A | 4/1996 | Goode et al. |
| 5,653,684 A | 8/1997 | Laptewicz et al. |
| 5,846,251 A | 12/1998 | Hart |
| 6,074,339 A | 6/2000 | Gambale et al. |
| 6,196,996 B1 | 3/2001 | Teirstein |
| 6,991,614 B2 | 1/2006 | Mcweeney et al. |
| 7,566,316 B2 | 7/2009 | McGuckin, Jr. et al. |
| 7,722,604 B2 | 5/2010 | Brown, III et al. |
| 7,824,367 B2 | 11/2010 | Accisano, III et al. |
| 7,993,329 B2 | 8/2011 | Howell et al. |
| 8,007,540 B2 | 8/2011 | Robertson |
| 8,333,000 B2 | 12/2012 | Huang et al. |
| 8,657,884 B2 | 2/2014 | Smouse |
| 8,676,349 B2 | 3/2014 | Stalker et al. |
| 2003/0195456 A1* | 10/2003 | Robertson ................ A61F 2/04 604/8 |
| 2007/0112420 A1 | 5/2007 | Laduca |
| 2007/0276466 A1* | 11/2007 | Lavelle .................... A61F 2/04 623/1.22 |
| 2008/0140101 A1 | 6/2008 | Carley et al. |
| 2010/0070047 A1 | 3/2010 | Smouse |
| 2011/0009950 A1 | 1/2011 | Grandfield et al. |
| 2014/0200462 A1 | 7/2014 | Stalker et al. |

OTHER PUBLICATIONS

Office action dated Jan. 3, 2012 for U.S. Appl. No. 12/559,946.
Office action dated Oct. 24, 2012 for U.S. Appl. No. 12/559,946.

* cited by examiner

CONVERTIBLE NEPHROURETERAL CATHETER

CROSS-REFERENCE TO RELATED APPLICATIONS

This application is a continuation-in-part of U.S. patent application Ser. No. 12/559,946, filed Sep. 15, 2009, entitled "Convertible Nephroureteral Catheter," which is a non-provisional of U.S. Provisional Application Ser. No. 61/096,902, filed Sep. 15, 2008, the contents of all of which are fully incorporated herein by reference.

FIELD

The present invention relates generally to catheters. More particularly, the present invention relates to a nephroureteral catheter.

BACKGROUND

Many patients experience the development of a stricture or blockage within the ureter of one or both kidneys. The ureter is the muscular tube that connects the kidney to the bladder. As urine is made by the kidney it drains into a central collecting system of the kidney and then travels though the ureter into the bladder. Patients can develop strictures, or blockages, of the ureter due to kidney stones, cancers, infections, trauma, and prior medical instrumentations. In rare instances, some children are born with blockages of one or both ureters. If untreated, the blockage will eventually lead to kidney failure.

Regardless the cause, the treatment for a blocked ureter is to relieve the blockage. Blockage removal is performed by inserting a long tube to connect the collecting system of the kidney to the bladder. This tube is called a stent and is placed through the ureter.

Stent insertion is typically performed by one of two methods. The stent may be inserted urologically. With this method, a scope is advanced through the urethra into the bladder. A wire is then inserted into the ureter in a retrograde fashion, using the scope to thread the wire. When the wire reaches the collecting system of the kidney, a plastic stent is inserted over the wire. The stent is a straight plastic tube that has a pigtail-shaped curl on each end. Once in place, the wire is removed and the scope is taken out of the bladder. One pigtail curl of the stent resides in the collecting system of the kidney and the other resides in the bladder. The straight portion of the stent traverses the ureter. This is performed using direct visualization with the scope and also with fluoroscopic guidance. The stent usually stays in for a period of approximately three months, at which point the stent is then swapped out for a new stent by the urologist using a similar technique.

The second method for insertion is to insert the stent percutaneously. This method is typically performed in stages. The right or left flank of the patient is sterilely prepared depending upon which kidney is to be accessed (sometimes both are accessed to treat bilateral blockages). Intravenous sedation is used. A small bore needle is used to puncture the collecting system of the kidney and contrast is injected allowing the complete visualization of the entire collecting system. The central portion is initially punctured with a small needle, and then a larger needle is used to puncture a smaller but safer area of the collecting system. A guidewire is threaded into the collecting system of the kidney and a pigtail drain, or nephrostomy catheter, is placed, sutured to the back, and hooked up to a bag for external drainage. Once the urine has cleared from bleeding, the patient is brought back to the angiography table, placed prone, and a wire is inserted through the catheter into the kidney. The catheter is then removed. The wire is threaded through the ureter into the bladder (across the stricture) and a nephroureteral catheter is placed.

A nephroureteral catheter is a long plastic tube that goes from the outside of the patient into the kidney's collecting system, through the ureter, and into the bladder. The catheter allows drainage of urine into the bladder and externally into a bag. The catheter typically stays in the patient for 7-10 days, at which time the patient is brought back to the angiography table and a wire is threaded through this tube into the bladder. The tube is removed and an internal stent is placed using fluoroscopic guidance. This is the same type of stent that is placed by the urologist working through the bladder. This can be a complex and difficult procedure.

SUMMARY

In accordance with the present invention, a nephroureteral catheter is provided that comprises a detachable portion such that when the detachable portion is removed, the catheter converts into an internal stent.

The catheter includes a tube having a circular cross section, a first end, a second end, a first retention feature near the first end, and a second retention feature near the second end. The catheter also comprises a detachable portion, wherein the detachable portion is in fluid communication with and is removably attachable to the tube at the second end, an inner tube comprising at least one lumen, wherein the inner tube is removably insertable into both the tube and the detachable portion, and a wire extending through at least a portion of a lumen of the at least one lumen of the inner tube. A portion of the wire is attached to the tube.

The convertible nephroureteral catheter eliminates the step of removing a nephroureteral catheter and placing a new internal stent into a patient. Because a step is eliminated, the convertible nephroureteral catheter saves time. Instead of a physician having to take steps such as sterile prep to place a new catheter inside a patient, the physician need only unlock the hub of the convertible nephroureteral catheter to detach the external portion of the catheter. Money is also saved since one less catheter will be required. In addition, other supplies such as wires, sheaths, and other equipment needed to place a typical internal catheter will be spared. The patient will only be subjected to minimal, if any, radiation from fluoroscopy.

The convertible nephroureteral catheter will also result in less patient discomfort, again due to minimal manipulation because less steps are required. With previous stent insertion procedures, local and IV sedation and nursing monitoring were required.

Patients will not require sedation for the process of removing the removable portion of the convertible nephroureteral catheter. The new procedure for transforming the convertible nephroureteral catheter may be performed at bedside.

The convertible nephroureteral catheter allows for the catheter insertion process to be a single step instead of a multiple-step process. The ability to insert a catheter percutaneously with a single step might provide an advantage over urological insertion, as they will both now require only a single step for insertion, yet using the convertible nephroureteral catheter will not require the general anesthesia required by urological insertion.

BRIEF DESCRIPTION OF THE DRAWINGS

Various embodiments are described herein with reference to the following drawings. Certain aspects of the drawings are depicted in a simplified way for reason of clarity. Not all alternatives and options are shown in the drawings and, therefore, the invention is not limited in scope to the content of the drawings. In the drawings.

DETAILED DESCRIPTION

Figure 1:
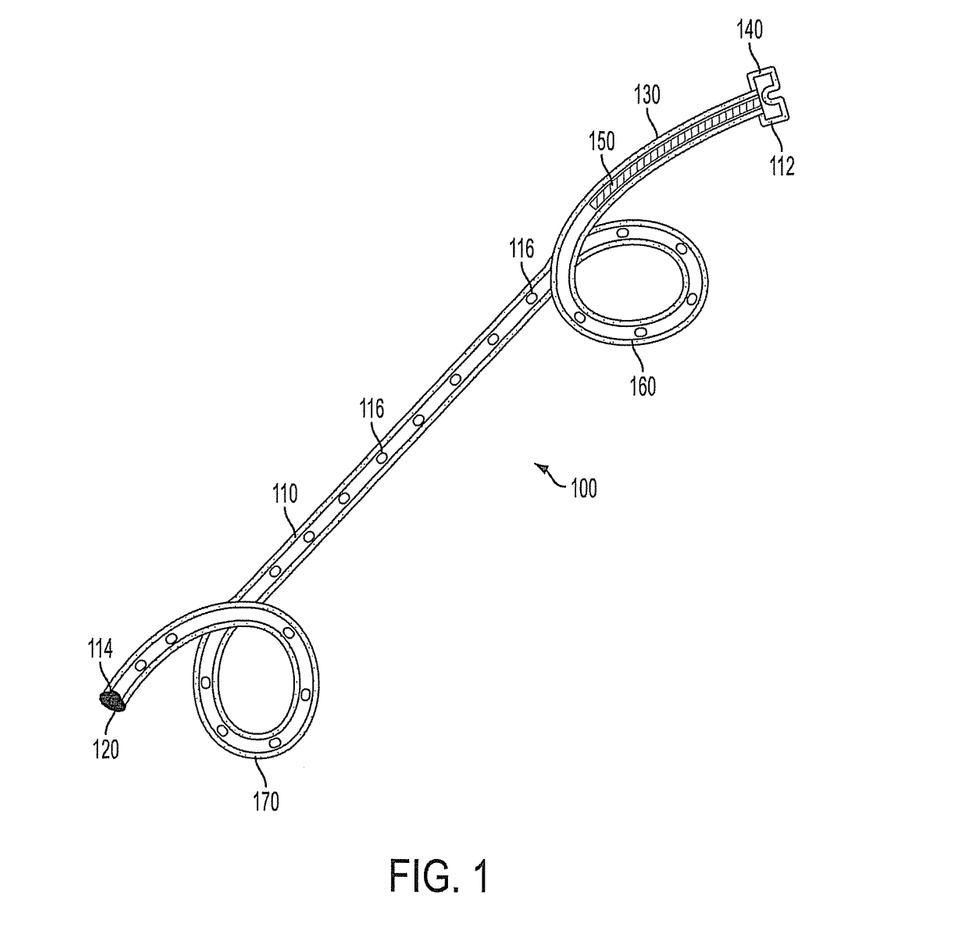
FIG. 1 depicts a nephroureteral catheter, in accordance with example embodiments.

FIG. 1 depicts a catheter 100, in accordance with example embodiments. Catheter 100 is provided for use as a nephroureteral catheter and is configured to be placed within a patient.

Figure 8:
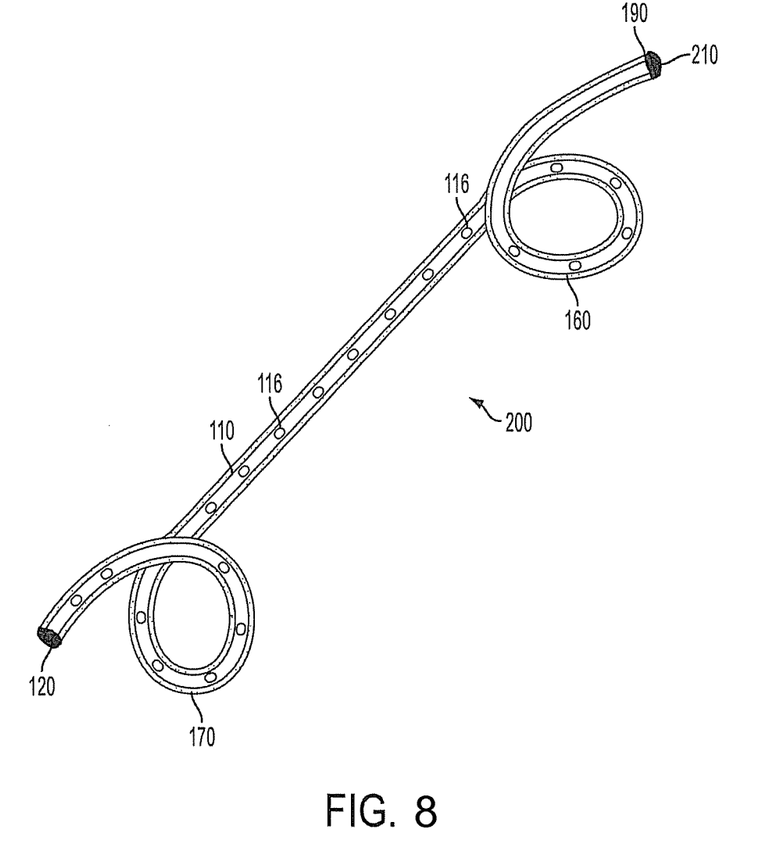
FIG. 8 depicts a stent that remains after a detachable portion has been removed, in accordance with example embodiments.

Catheter 100 allows for the drainage of urine into the bladder and externally into a bag. Catheter 100 includes a tube 110 having a circular cross section 120, a detachable portion 130, a locking mechanism 140, an inner tube 150, a first pigtail curl 160, a second pigtail curl 170, and a marker 190. Catheter 100 also includes a first end 112, a second end 114, and a plurality of holes 116. When detachable portion 130 is attached to the catheter, catheter 100 is a nephroureteral catheter. When detachable portion 130 is removed from the catheter, the catheter becomes a stent 200, as shown in FIG. 8.

Tube 110 may be flexible. The tube 110 has a hollow interior or lumen to allow for fluids to flow through the tube. A plurality of holes 116 extend through tube 110 so that fluids may flow into or out of tube 110 through the holes. Tube 110 is of sufficient length so that it extends from the outside of the patient into the kidney, through the ureter and into the bladder.

First pigtail curl 160 and second pigtail curl 170 serve the purpose of retaining or keeping tube 110 in the proper position within the patient. First pigtail curl 160 is located near first end 112 and second pigtail curl 170 is near second end 114, so that first pigtail curl 160 lies within the collecting system of the kidney and second pigtail curl 170 lies within the bladder. Each curl serves as a retention feature and ensures tube 110 will not move out of the ureter, because each curl is too large to pass through the ureter. Second pigtail curl 170 enters the ureter in a straight position, but the material of tube 110 at the section of second pigtail curl room to bend, or once it has exited the ureter.

Figure 2:
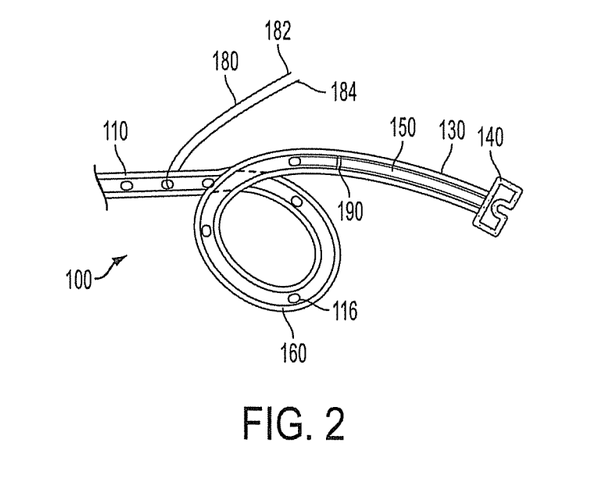
FIG. 2 depicts a detachable portion of the nephroureteral catheter of FIG. 1, in accordance with example embodiments.

First pigtail curl 170 is such that it will bend into the curl position shown in FIG. 1 after the tube has curl enters the kidney in the straight position as well, and may also bend into the curl position once in place. However, to help first pigtail curl bend to the proper position, a string 180 may be pulled through a hole of the plurality of holes 116, as shown in FIG. 2, and the string may be manually pulled on both ends 182, 184 until first pigtail curl is set in place. Thereafter, string 180 may be manually removed by pulling one of ends 182, 184. String 180 may be a suture. Alternatively, string 180 may be a number of other materials.

Locking mechanism 140 may be a number of locking mechanisms currently used in the art. Locking mechanism closes off detachable portion 130 of tube 110, and may be manually opened and removed to access any of detachable portion 130, inner tube 150, or tube 110.

Detachable portion 130 may be made from the same material as tube 110. Detachable portion 130 may be flush with tube 110 at marker 190. Detachable portion 130 comprises a hollow section within which inner tube 150 may slide through. Inner tube may extend through a portion of tube 110, as shown in FIG. 2. Inner tube 150 comprises a hollow interior to allow for fluid to flow through the interior of inner tube 150. Fluid is exchanged between tube 110 and inner tube 150 through the hollow interior of inner tube 150. Tube 110 also comprises at least a portion of a hollow section within which tube portion 150 may slide through. In some example embodiments, the hollow portions of both detachable portion 130 and tube 110 may be sized such that when inner tube portion 150 is inside the hollow portions of the detachable portion 130 and tube 110, there is a friction seal between the exterior surface of tube portion 150 and the walls of the hollow portions. However, tube portion 150 may be attached to tube 110 in a number of other ways. For example, in an alternative embodiment, inner tube 150 may comprise threads on its exterior surface that correspond to threads along the walls of the hollow interior of tube 110, and thus to remove inner tube 150 from tube 110, inner tube 150 must be unscrewed from tube 110. In another alternative embodiment, detachable portion 130 may comprise a smaller circumference than tube 110 such that detachable portion 130 may also fit within the hollow portion of tube 110, for example 2 or 3 mm into tube 110. Thus when inner tube 150 is in place within both tube 110 and detachable portion 130, inner tube 150 pushes outward on detachable portion 130, which in turn presses on tube 110, resulting in a tighter fit. In this embodiment, detachable portion 130 may still be manually removed from tube 110 after the removal of inner tube 150 from tube 110.

Detachable portion 130 may be manufactured as part of catheter 100. When attached to catheter 100 and in place inside a patient, detachable portion 130 extends from the center of the kidney to an exit in the back of the patient, ending with locking mechanism 140, which is located outside the patient's body.

Figure 3:
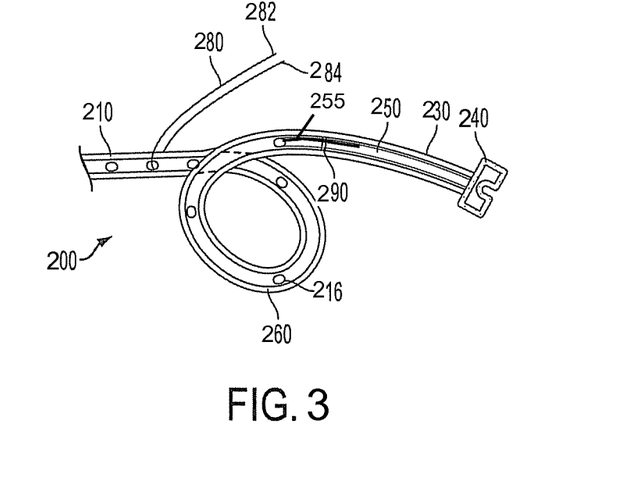
FIG. 3 depicts a detachable portion of the nephroureteral catheter of FIG. 1, in accordance with example embodiments.

In another example embodiment, an inner tube portion 250 and a wire 255 may extend through both detachable portion 230 and the tube 210, as shown in FIG. 3. In this embodiment, inner tube portion 250 comprises a hollow interior or lumen 252 to allow for fluid to flow therethrough. Thus, fluid is exchanged between tube 210 and inner tube portion 250 through the hollow interior of inner tube portion 250. Tube 210 also comprises at least a portion of a hollow section within which tube portion 250 may slide through.

Detachable portion 230 may be manufactured as part of catheter 200. When attached to catheter 200 and in place inside a patient, detachable portion 230 extends from the center of the kidney to an exit in the back of the patient, ending with locking mechanism 240, which is located outside the patient's body.

Figure 4A:
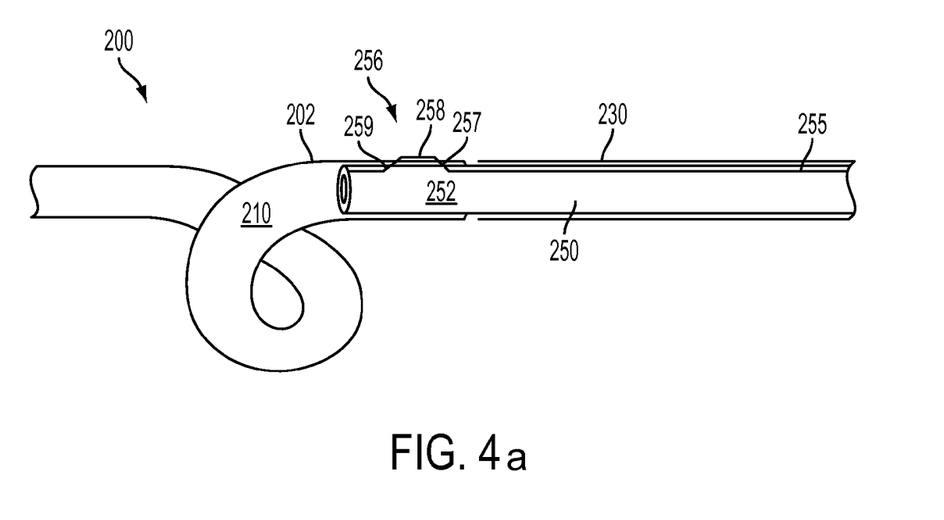
FIG. 4a depicts a detailed view of a removable attachment system, in accordance with example embodiments.

FIG. 4a shows a detailed view of the catheter 200 of FIG. 3. Wire 255 is shown to extend through lumen 252 of inner tube 250. Wire 255 may extend from locking mechanism 240 in the distal direction through the entire length of lumen 252 of inner tube 250, in some example embodiments. In other example embodiments, however, wire 255 may only extend partially through lumen 252 of inner tube 250. Wire 255 may comprise a portion 256 that extends through and over the exterior of tube 210, at a region where tube 210 overlaps the inner tube 250, thereby affixing tube 210 and inner tube 250. The portion 256 may comprise a first angled section 257 that extends from within lumen 252 of inner tube 250, through the wall of tube 210 and an outer surface 202 of tube 210, a generally flattened section 258 that extends above outer surface 202 of tube 210, and a second angled section 259 that extends from generally flattened section 258, through the wall of tube 210 back into lumen 252 of inner tube 250.

The wire 255 may be affixed to and then removed at the locking mechanism 240 to disconnect the distal section of inner tube 250 from tube 210, rendering the catheter 200 a stent, as will be described with further detail below. The locking mechanism may comprise a luer lock, for example. Other locking mechanisms may also be envisioned. Such a locking mechanism may be affixed via any of a number of bonding or fastening methods.

Wire 255 may comprise a material that has sufficient tensile strength to hold inner tube 250 and tube 210 together, such as a metallic composite material. Example metallic composite materials that may be used are stainless steel, Elgiloy, a nickel cobalt alloy (e.g., MP35N), or a nickel titanium alloy (e.g., Nitinol), for example.

To connect the detachable portion 230 to tube 210, wire 255 may be sent through inner tube 250, which may contain one or more lumens.

Figure 4B:
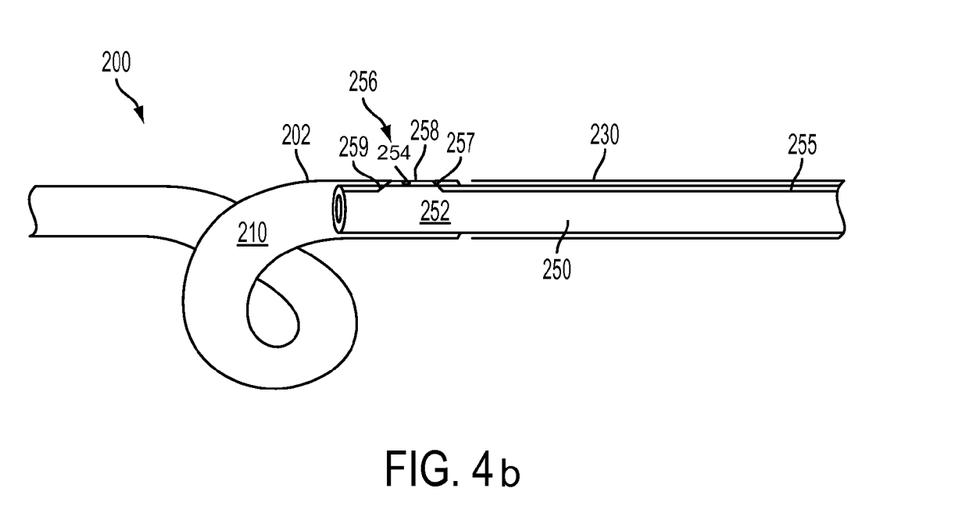
FIG. 4b depicts a detailed view of a removable attachment system, in accordance with example embodiments.

In an alternative embodiment shown in FIG. 4b, instead of wire 255 traveling through the wall of tube 210 and extending beyond exterior 202 of tube 210 to affix the inner tube 250 within the tube 210, wire 255 may continue over a separate wire segment 254 which is normal to wire 255 and within lumen of tube 210. The separate wire segment 254 may be fused into the wall of tube 210 while providing a small area for passage of wire 255 and a large area for passage for inner tube 252. The wire 255 may continue its path over the separate wire segment 254, remaining entirely within the lumen of tube 210, and completing second angled section 259 to return into lumen 252 of inner tube 250.

Figure 5A:
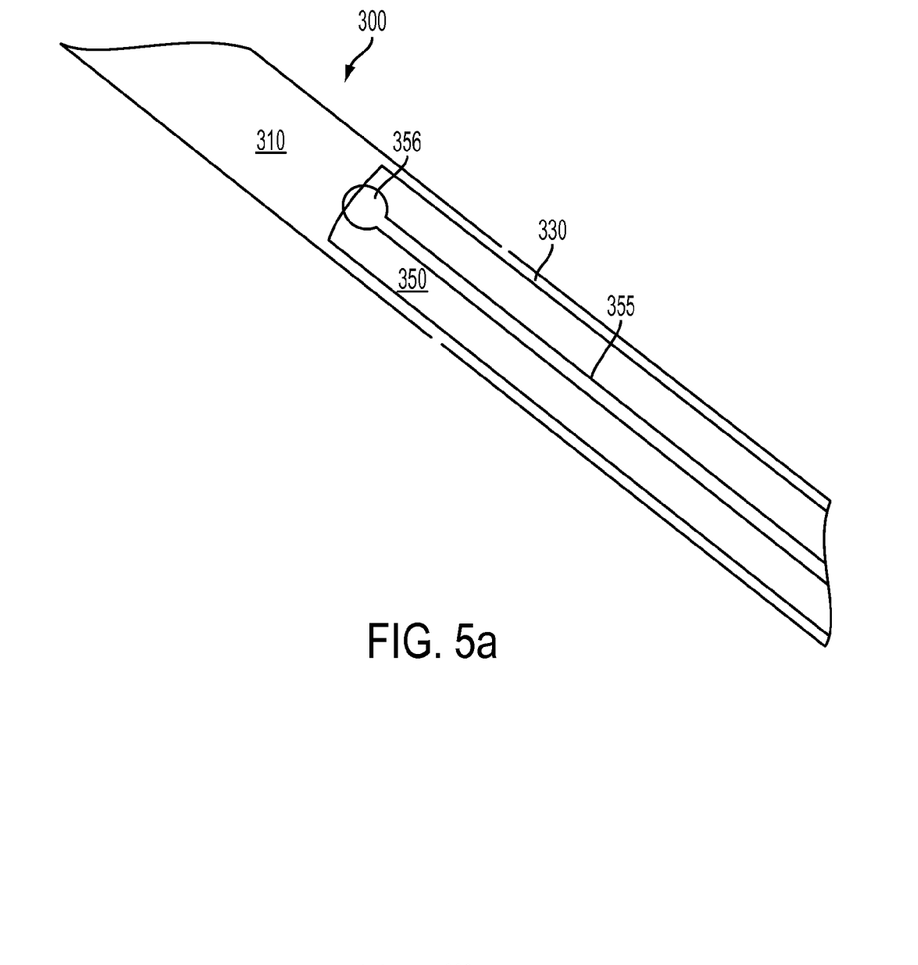
FIGS. 5a-5b depict detailed views of a removable attachment system, in accordance with example embodiments.
Figure 5B:
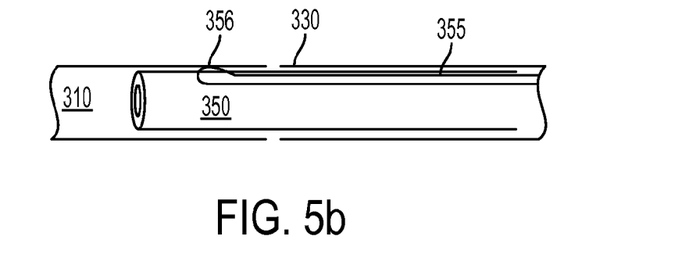

FIGS. 5a-5b show detailed top and side views of a wire 350 within a tube 310, in accordance with an example embodiment. The tube 310 may take the same form as or may be similar in form to the tube 110 or 210 described with reference to FIGS. 1-4. A detachable portion 330 and an inner tube 350 are also shown, and may take the same form as or may be similar in form to the detachable portion 130 or 230 and the inner tube 150 or 250 described with reference to FIGS. 1-4. In the embodiment shown in FIGS. 5a-5b, a wire 355, comprising a metal band, may be used to removably attach the detachable portion 330 to the tube 310. An engagement portion 356 of the wire 355 is shown to engage into an interior wall 305 of the catheter 300. The engagement portion 356 may comprise a bump, hill, or other pronounced surface extending above the surface of the remaining wire 355.

Figure 6:
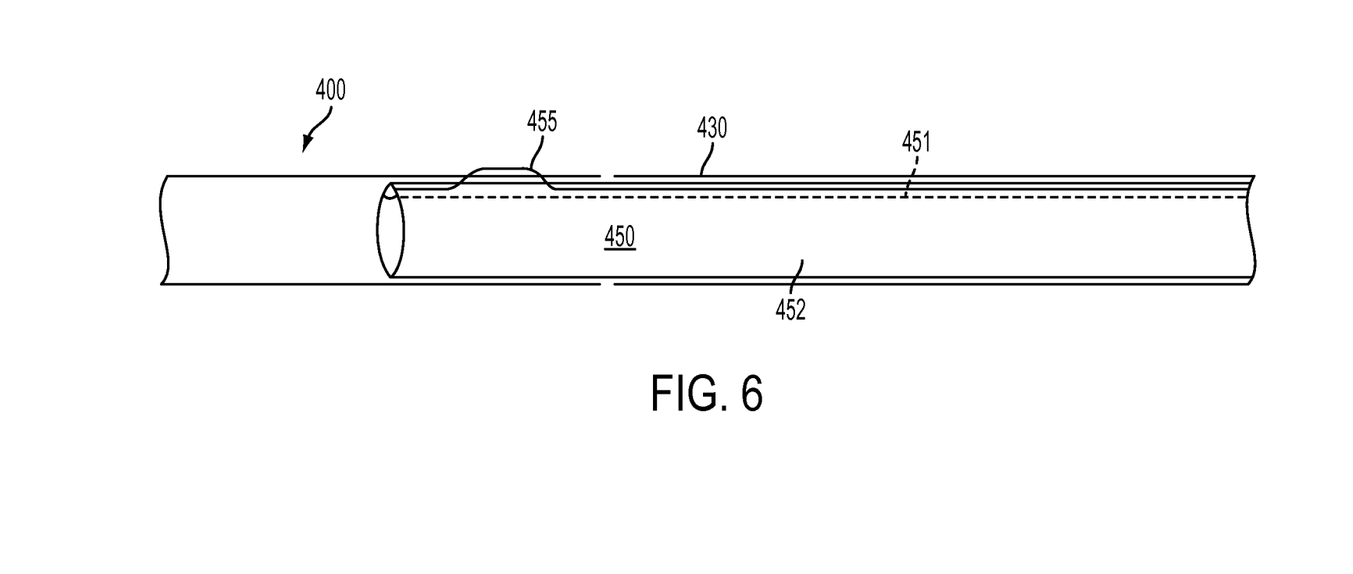
FIG. 6 depicts a detailed view of a removable attachment system, in accordance with example embodiments.

FIG. 6 shows a detailed cross-sectional side view of a wire 450 within a catheter 400, in accordance with an example embodiment. The catheter 400 may take the same form as or may be similar in form to catheter 100 or 200 described with reference to FIGS. 1-4. A detachable portion 430 is also shown, and may take the same the detachable portion 130 or 230 described with reference to FIGS. 1-4.

An inner tube 450 may comprise two lumens, first lumen 451 and second lumen 452. First lumen 451 may comprise a wall to separate first lumen 451 from second lumen 452. A wire 455, which may take the form of either wire 255 or wire 355, may run through first lumen 451 and thus be isolated within lumen 451 so as not to interfere with second lumen 452. Second lumen 452 may serve as a wire guide or stent straightening lumen. The dual lumen feature of inner tube 450 permits the use of an isolated access pathway (second lumen 452) to be used for device tooling such as a wire guide or stent straightener without risk of disrupting wire 455 located within lumen 451. First lumen 451 provides a protective safeguard against dislodgement of wire 455 during implantation of the catheter within patient and during the corresponding exchange of catheter tooling during intervention. Fluid may be exchanged between catheter 400 and inner tube 450 via both first lumen 451 and second lumen 452.

Figure 7:
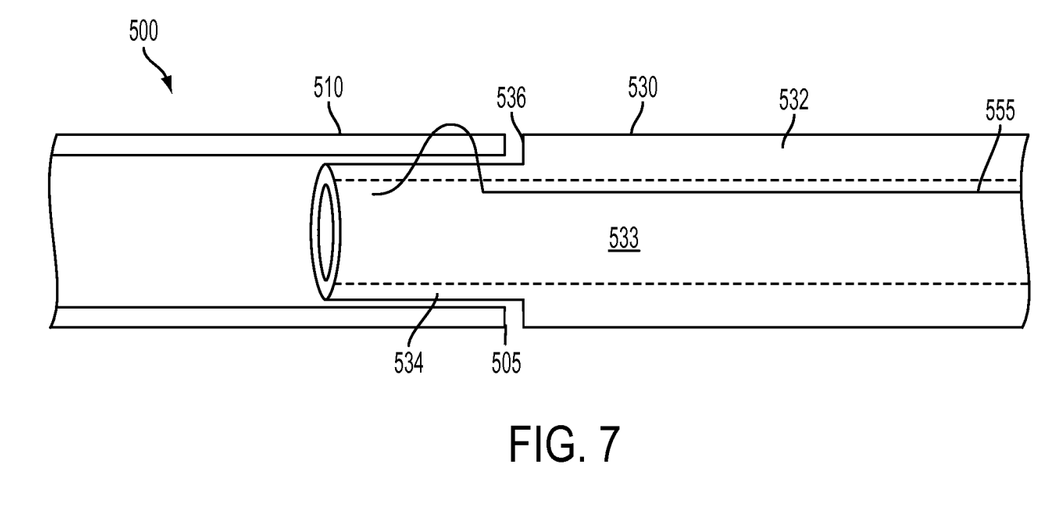
FIG. 7 depicts a detailed view of a removable attachment system, in accordance with example embodiments.

FIG. 7 shows a detailed cross-sectional side view of an example detachable portion 530 of a catheter 500, according to an example embodiment. The catheter 500 may take the same form as or may be similar in form to catheter 100 or 200 described with reference to FIGS. 1-4. The catheter 500 may comprise a tube 510, which may take the same form as or may be similar in form to tube 110 or 210 described with reference to FIGS. 1-4.

Detachable portion 530 may comprise a first tube portion 532, a second tube portion 534, and a transition 536 from the first tube portion 532 to the second tube portion 534. Transition 536 may take the form of a step and may comprise about a 90 degree transition. A lumen 533 may extend through both the first tube portion 532 and the second tube portion 534 as shown, and may comprise the same diameter through both portions. Transition 536 may mate with or abut an end 505 of catheter 500. Second tube portion 534 comprises a smaller diameter than the first tube portion 532, and is sized and shaped to fit within the lumen of the catheter 500. Such a design for detachable portion 530 renders having an additional inner tube, such as inner tubes 150 and 250, for example, unnecessary.

FIG. 8 shows a perspective view of a stent 200 that remains after the detachable portion has been removed. Stent 200 comprises the same tube 110 as catheter 100, with first pigtail curl 160 and second pigtail curl 170 untouched within the body of the patient. Detachable portion 130, inner tube 150, and locking mechanism 140 have been removed. A new end 210 is at marker 190.

In operation, the right or left flank of the patient is sterilely prepared depending upon which kidney is to be accessed. Intravenous sedation is used. A small bore needle is used to puncture the collecting system of the kidney and contrast is injected allowing the complete visualization of the entire collecting system. The central portion is initially punctured with a small needle, and then a larger needle is used to puncture a smaller but safer area of the collecting system. A guidewire is threaded into the collecting system of the kidney and a pigtail drain, or nephrostomy catheter, is placed, sutured to the back, and hooked up to a bag for external drainage.

Once the urine has cleared from bleeding, the patient is brought back and a wire is inserted through the catheter into the kidney and the catheter is removed. The wire is threaded through the ureter into the bladder (across the stricture) and catheter 100 is placed. Pigtail curls 160, 170 are curled to their proper position. The catheter typically stays in the patient for 7-10 days, at which time the patient is brought back.

At this point, if the physician desires to exchange the catheter 100 for a stent 200, the physician will unlock locking mechanism 140, and will remove the locking mechanism to access inner tube 150. The physician will then manually pull inner tube 150 through the hollow portion of tube 110 toward first end 112, until inner tube 150 has been pulled past marker 190 and is no longer within the hollow portion of tube 110.

In another example embodiment, wherein a wire is used, such as described with reference to FIGS. 3-7, the physician will first release the locking mechanism maintaining connection with a wire, such as wire 255, 355, 455, or 555. The wire may be released using a method such as unscrewing a cap, for example. In such an example embodiment, the unscrewed cap (which has been attached to the wire at the proximal luer hub) disengages the wire from the catheter (e.g., catheters 310 and 400) by pulling the cap away from the hub and fully withdrawing the wire from the inner tube (e.g., inner tubes 250, 350, 450). Once the wire has been removed, the detachable portion (e.g., detachable portions 330 and 530) and the inner tube may now be fully withdrawn from the patient's body, converting the catheter into a stent (e.g., stent 200).

Once inner tube 150 has been removed from tube 110, detachable portion 130 is no longer attached to tube 110 and both detachable portion 130 and inner tube 150 may be removed from the patient's body. Once detachable portion 130 and inner tube 150 are removed, catheter 100 becomes a stent 200, as shown in FIG. 3. This is same type of stent that would typically be placed by the urologist working through the bladder. Stent 200 now comprises a new end 210 that is located at marker 190.

An example of when the convertible nephroureteral catheter may be used is a situation in which a patient has a blockage of the ureter and presents with hydronephrosis (dilation of the kidney's collecting system) and hydroureter (dilation of the ureter). The patient has a device inserted through the flank, into the collecting system, and through the ureter into the bladder. The device will be left open to external drainage until the urine clears from infection or bleeding. When the urine has cleared, the external portion of the convertible nephroureteral catheter 100 will be detached, converting the catheter into an internal stent. From this point forward, the stent will drain urine directly from the kidney to the bladder. The internal stent will remain in place until it is ready to be removed or replaced.

Another example of use is when a patient recently passed a kidney stone and the ureter is temporarily inflamed and blocked. The convertible nephroureteral catheter is inserted in the same manner described above. In this situation, however, the catheter is in place temporarily until the inflammation improves; once this is confirmed, the entire catheter is removed by pulling it out of the flank with contrast injection under fluoroscopy. In this situation the detachable portion is not detached. However, the catheter may also be left in place as an internal stent, and the detachable portion removed, depending on the clinical need.

Another example of use is when a patient has leakage from the ureter due to trauma, instrumentation, stone removal, cancer, or another reason, and internal and external urine diversion is necessary. In this case, convertible nephroureteral catheter 100 is placed in the patient and urine is allowed to drain externally. When there is improvement in the leakage and the catheter is converted to an internal stent by removing detachable portion 130, internal urine diversion is allowed for a longer period of time. The stent 500 will be removed at a later date after the leak is resolved.

It will thus be seen that certain changes may be made in the above constructions without departing from the spirit and scope of the invention. It is intended that all matter contained in the above description or shown in the accompanying drawings shall be interpreted as illustrative and not in a limiting sense.

We claim:

1. A method for converting a catheter into a stent comprising:
   providing a catheter having a tube comprising a first end, a second end, a first retention feature near the first end and a second retention feature near the second end, and a detachable portion, wherein the detachable portion is in fluid communication with and is removably attachable to the tube at the second end, and the second retention feature comprises a curled portion of the tube;
   wherein the tube and the detachable portion together form a nephroureteral catheter;
   percutaneously implanting the nephroureteral catheter into the kidney so that the first retention feature is in the bladder, the second retention feature is in the kidney, and the detachable portion is external to the patient;
   allowing the urine to drain;
   removing the detachable portion from the catheter to convert the catheter into an internal stent such that the curled portion of the tube is retained in the kidney; and
   retaining the implanted nephroureteral catheter in the kidney and the bladder for 7-10 days prior to removing the detachable portion from the catheter to convert the catheter into an internal stent.

2. The method of claim 1, further comprising:
   providing an inner tube that extends through at least a portion of both the tube and the detachable portion and comprises at least one lumen;
   extending a wire through at least a portion of the at least one lumen of the inner tube; and
   attaching a portion of the wire to the tube;
   wherein removing the detachable portion comprises removing the wire and the inner tube from the tube.

3. The method of claim 1, further comprising:
   providing a locking mechanism at a first end of the detachable portion, wherein the locking mechanism is configured to open and close; and
   closing the locking mechanism to prevent access to an interior of the detachable portion.

4. The method of claim 1, further comprising:
   positioning the catheter in a patient by creating an incision in the patient at a surgical site and inserting the catheter through the incision.

5. The method of claim 4, wherein the surgical site is a flank of the patient to access one or more of a urethra, a bladder, a ureter, and a kidney via the flank.

6. The method of claim 4, further comprising:
   attaching the catheter to tubing exterior to the patient.

7. The method of claim 4, wherein removing the detachable portion comprises removing the detachable portion from the patient.

8. The method of claim 1, wherein the method is used to provide or monitor treatment for a disorder of the kidney or bladder.

9. The method of claim 1, wherein the nephroureteral catheter is percutaneously implanted into the kidney so that at least a portion of the detachable portion is within the patient, and wherein removing the detachable portion from the catheter comprises withdrawing the detachable portion from the patient.

10. The method of claim 1, wherein allowing urine to drain comprises draining the urine through the percutaneously implanted nephroureteral catheter into an external container.

11. The method of claim 1, wherein allowing urine to drain comprises allowing the urine to drain internally from the kidney to the bladder after the detachable portion is removed.

12. A method for converting a catheter into a stent comprising:
   providing a catheter having a tube comprising a first end, a second end, a first retention feature near the first end and a second retention feature near the second end, and a detachable portion, wherein the detachable portion is in fluid communication with and is removably attachable to the tube at the second end, and the second retention feature comprises a curled portion of the tube;

wherein the tube and the detachable portion together form a nephroureteral catheter;

percutaneously implanting the nephroureteral catheter into the kidney so that the first retention feature is in the bladder, the second retention feature is in the kidney, and the detachable portion is external to the patient;

allowing the urine to drain; and removing the detachable portion from the catheter to convert the catheter into an internal stent such that the curled portion of the tube is retained in the kidney; and wherein allowing urine to drain comprises draining the urine through the percutaneously implanted nephroureteral catheter into an external container.

13. The method of claim 12, further comprising:

providing an inner tube that extends through at least a portion of both the tube and the detachable portion and comprises at least one lumen;

extending a wire through at least a portion of the at least one lumen of the inner tube; and attaching a portion of the wire to the tube;

wherein removing the detachable portion comprises removing the wire and the inner tube from the tube.

14. The method of claim 12, further comprising:

providing a locking mechanism at a first end of the detachable portion, wherein the locking mechanism is configured to open and close; and closing the locking mechanism to prevent access to an interior of the detachable portion.

15. The method of claim 12, further comprising:

positioning the catheter in a patient by creating an incision in the patient at a surgical site and inserting the catheter through the incision.

16. The method of claim 15, wherein the surgical site is a flank of the patient to access one or more of a urethra, a bladder, a ureter, and a kidney via the flank.

17. The method of claim 15, further comprising:

attaching the catheter to tubing exterior to the patient.

18. The method of claim 15, wherein removing the detachable portion comprises removing the detachable portion from the patient.

19. The method of claim 12, wherein the method is used to provide or monitor treatment for a disorder of the kidney or bladder.

20. The method of claim 12, wherein the nephroureteral catheter is percutaneously implanted into the kidney so that at least a portion of the detachable portion is within the patient, and wherein removing the detachable portion from the catheter comprises withdrawing the detachable portion from the patient.

21. The method of claim 12, wherein allowing urine to drain comprises allowing the urine to drain internally from the kidney to the bladder after the detachable portion is removed.

* * * * *